United States Patent [19]

Plummer

[11] Patent Number: 4,528,408
[45] Date of Patent: Jul. 9, 1985

[54] TRANS-3-SUBSTITUTED-1-INDANOL AND INSECTICIDAL ESTER DERIVATIVES

[75] Inventor: Ernest L. Plummer, Yardley, Pa.

[73] Assignee: FMC Corporation, Philadelphia, Pa.

[21] Appl. No.: 660,569

[22] Filed: Oct. 16, 1984

Related U.S. Application Data

[60] Continuation of Ser. No. 445,136, Nov. 26, 1982, abandoned, which is a division of Ser. No. 245,484, Mar. 19, 1981, Pat. No. 4,362,744.

[51] Int. Cl.³ .................................................. C07C 33/34
[52] U.S. Cl. ............................................................. 568/808
[58] Field of Search ................................................. 568/808

[56] References Cited

PUBLICATIONS

Schering, "Chemical Abstracts", vol. 52, pp. 20107–20108, and 11943c, (1957).
Tsybib et al., "Chemical Abstracts", vol. 71, (1969), p. 38146f.
Barltrop et al., "Chemical Abstracts", vol. 52, p. 2690, (1957).

*Primary Examiner*—Werren B. Lone
*Attorney, Agent, or Firm*—Robert M. Kennedy; H. Robinson Ertelt; Robert L. Andersen

[57] ABSTRACT

Disclosed are novel compounds of the formula

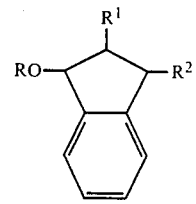

in which $R^1$ is hydrogen or methyl; $R^2$ is phenyl or phenylmethyl either of which is optionally ring substituted with lower alkyl or halogen; R is hydrogen, a tetramethylcyclopropanecarbonyl group, a 1-(substitutedphenyl)-2-methylpropylcarbonyl group, a 1-(4-ethoxyphenyl)-2,2-dichlorocyclopropanecarbonyl group, or a substitutedvinylcyclopropanecarbonyl group; and, with respect to the indanyl substituents, the 1,3-trans isomer is present in an isomeric excess over the corresponding 1,3-cis isomer. The compounds wherein R is other than hydrogen are insecticides, and the compounds wherein R is hydrogen are insecticide intermediates.

4 Claims, No Drawings

TRANS-3-SUBSTITUTED-1-INDANOL AND INSECTICIDAL ESTER DERIVATIVES

This application is a continuation of application Ser. No. 445,136, filed Nov. 26, 1982 and now abandoned which is a division of application Ser. No. 245,484, filed Mar. 19, 1981 now U.S. Pat. No. 4,362,744.

The present application is directed to a novel alcohol for use in preparing cyclopropanecarboxylate and related insecticides, to insecticides employing this alcohol, and to an insecticidal method and composition. More particularly, the invention is directed to a 3-substituted-1-indanol wherein the 1,3-trans isomer is present in an isomeric excess over the corresponding 1,3-cis isomer, and to insecticidal esters thereof.

Pyrethrins, naturally occurring extracts of chrysanthemum flowers, have long been of interest as insecticides. Since elucidation of the structures of these compounds, synthesis efforts have been directed toward preparation of related compounds having enhanced insecticidal activity and improved stability toward air and light. Since a prerequisite for insecticidal activity of pyrethroids is the presence in one molecule of an appropriate acid moiety and an appropriate alcohol moiety, research in the art has been directed toward novel acid and/or alcohol radicals. Noteworthy advances in the area of alcohol research were the discovery of 5-benzyl-3-furylmethyl alcohol, then of the more photostable 3-phenoxyphenylmethyl alcohol (see *Synthetic Pyrethroids*, ACS Symposium Series, No. 42, M. Elliott, Ed., American Chemical Society, Washington, D.C. 1977, Chapter 1). Similarly significant advances have been made in pyrethroid acid research. The commercial insecticide permethrin, the common name for 3-phenoxyphenylmethyl 3-(2,2-dichloroethenyl)-2,2-dimethylcyclopropanecarboxylate, exemplifies use of both newer acid and alcohol moieties in a single compound.

The present invention provides a novel indanyl alcohol and certain insecticidal pyrethroid esters of it.

In this application, the term "lower" as applied to an aliphatic hydrocarbon group means having 1 to 6 carbon atoms, preferably 1 to 4 carbon atoms. The term "halo" or "halogen" means bromine, chlorine or fluorine. The term "perhaloalkyl" means an alkyl group of 1 or 2 carbon atoms completely substituted with independently selected halogen atoms. The term "insecticide" is used in its broadest sense and includes compounds possessing activity against true insects, acarids, and other household, veterinary or crop pests of the phylum Arthropoda. "Isomeric excess" is the percent excess of one geometric isomer over the corresponding other geometric isomer in a mixture containing cis and trans isomers of a compound, in accordance with the formula % Isomeric Excess=$(X-Y)/(X+Y) \cdot 100$ where X is the concentration of the more abundant isomer in the mixture, and Y is the concentration of the less abundant isomer, it being understood, of course, that where only one of the two geometric isomers is present, that isomer is present in an isomeric excess of 100%. The term "trans" or the designation "t" when used to denote relative configuration of substituents for a 3-substituted-1-indanol or a 3-substituted-1-indanyloxy moiety, means the configuration of the substituent at C-3 of the indanyl ring is trans relative to that of the oxygen substituent at C-1 of the indanyl ring, and does not pertain to the relative configuration of any substituent at C-2 of the ring. These definitions are applicable throughout the specification and claims except where a contrary meaning is clearly indicated.

The 3-substituted-1-indanyl compounds of this invention have the general formula

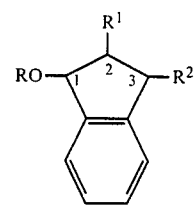

in which $R^1$ is hydrogen or methyl; $R^2$ is phenyl or phenylmethyl optionally ring substituted with lower alkyl or halogen, for example, fluorine or chlorine; R is hydrogen, 2,2,3,3-tetramethylcyclopropanecarbonyl, 1-(substitutedphenyl)-2-methylpropyl-1-carbonyl, particularly 1-(4-chlorophenyl)-2-methylpropyl-1-carbonyl, 1-(4-ethoxyphenyl)-2,2-dichlorocyclopropanecarbonyl, or an ethenylcyclopropanecarbonyl group of the formula:

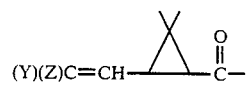

wherein Y and Z, the same or different, are hydrogen, halogen, lower alkyl, perhaloalkyl, phenyl which may be substituted with halogen or lower alkyl, or phenylthio which may be substituted with halogen or lower alkyl, with the proviso that one of Y and Z is other than hydrogen; and, with respect to the substituents on the indanyl moiety, the 1,3-trans isomer is present in an isomeric excess over the 1,3-cis isomer.

The alcohols of this present invention are the compounds of formula I in which R is hydrogen. Alcohols of especial interest are those wherein $R^1$ is hydrogen, $R^2$ is optionally substituted phenylmethyl, and the trans isomer is present in an isomeric excess of at least 50%. The group $R^2$ is advantageously unsubstituted phenylmethyl, but compounds in which the phenyl ring is substituted in 1 or 2 positions with methyl, chlorine, or fluorine, particularly fluorine, are also of particular interest. In a preferred embodiment, the alcohol consists essentially of the trans isomer.

The insecticidal compounds are those of formula I in which R is other than hydrogen. One subgenus of particular interest comprises the compounds wherein R is the group of formula II, and one of Y and Z is halogen, especially chlorine or bromine, and the other is halogen, preferably the same, or a perhaloalkyl group such as trihalomethyl, especially trifluoromethyl. Superior insecticidal activity is shown by the compounds of this subgenus having a preferred alcohol moiety, for example, the alcohol wherein $R^1$ is hydrogen, $R^2$ is phenylmethyl which may be substituted in the phenyl ring with lower alkyl or halogen such as fluorine or chlorine, particularly fluorine, and the trans isomer is present in an isomeric excess of at least 50%. In a preferred embodiment, the alcohol moiety of the insecticidal compound consists essentially of the trans isomer.

The acid moiety of formula II itself has cis and trans isomeric forms. The carbonyl group at C-1 and the ethenyl group at C-3 of the cyclopropane ring may be either cis or trans with respect to each other. Preparation of compounds having this acid residue will usually yield a mixture of these isomers, designated herein cis,-trans, in which the ratio of cis to trans may vary over a wide range. In the pyrethroid insecticide art it is known there may be substantial differences in the level of insecticidal activity between cis-cyclopropanecarboxylates and trans-cyclopropanecarboxylates. In general, for the compounds of the present invention having the acid moiety of formula II, compounds having the cis acid moiety are usually more active than the corresponding trans compounds, and also more active than the cis,trans mixture. Also, for the cis-acid containing compounds, those having the R absolute configuration at C-1 of the cyclopropane ring are usually more active than the corresponding compounds having the S configuration, and also more active than 1R,S mixtures. For purposes of this application, the designations cis and trans for the acid moiety of formula II are assigned in accordance with P. E. Burt, et al., *Pestic. Sci.*, 5, 791–799 (1974).

The compounds where Y is different from Z may also exist as E or Z isomers or as mixtures of E and Z isomers, designated E,Z, depending upon the spatial relationship of substituents on the β-carbon of the ethenyl group to the cyclopropane ring. Differences in activity may also occur with respect to these E and Z isomers.

Unless a contrary intent is specifically expressed, this invention embodies and includes compounds having the cis acid moiety, and those having the trans acid moiety, as well as the cis,trans mixtures, i.e., compounds wherein the cis to trans ratio is within the range of 0:100 to 100:0. Similarly, the individual E and Z isomers, as well as the mixtures, are contemplated by and within the scope of the invention. The various possible enantiomers and mixtures of them are also included within the scope of the invention.

3-Substituted-1-indanols optionally having a methyl group at C-2 may be prepared by routine synthesis methods involving types of chemical reactions and separation techniques known in the art. The schema below is illustrative of such methods.

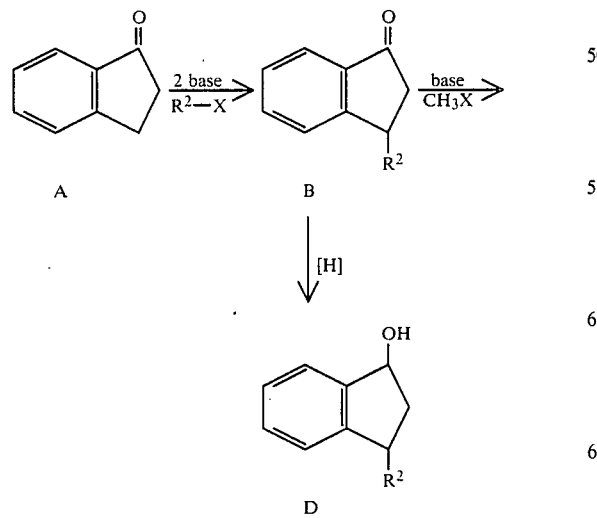

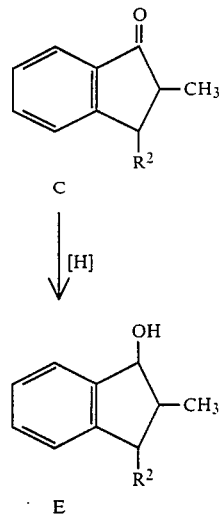

1-Indanone, A can be converted into its 3-substituted derivative B by a base effected displacement reaction in a manner similar to that reported by Trost and Latimer, J. Org. Chem., 42, 3212(1977). The 1-indanone is first converted into its dianion by treatment with at least two equivalents of a strong base such as lithium diisopropylamide. The dianion is then allowed to react with $R^2$—X, wherein X is a good leaving group such as a bromine or iodine atom, to give the 3-substituted-1-indanone B. Reduction of the 3-substituted-1-indanone, for example with aluminum isopropoxide/isopropanol, lithium aluminum hydride, borane/tetrahydrofuran, or ammonia borane, gives the corresponding 3-substituted-1-indanol, D, as a mixture of the cis and trans isomers. The desired trans isomer is then separated by chromatography. Trans-3-substituted-2-methyl-1-indanol may be prepared from the corresponding 3-substituted-1-indanone B by alkylation with $CH_3X$, followed by reduction of the resulting 2,3-disubstituted-1-indanone C to the corresponding 1-indanol E, and chromatographic separation of the 1,3-trans isomer from the cis,trans mixture, if necessary.

The novel insecticidal esters of this invention may be prepared by various methods including those exemplified below for the esters wherein R is the ethenylcyclopropanecarbonyl group of formula II.

Method A:

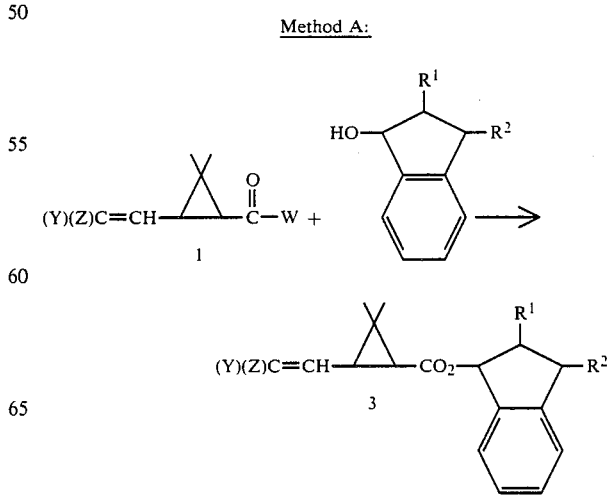

-continued

Method B:

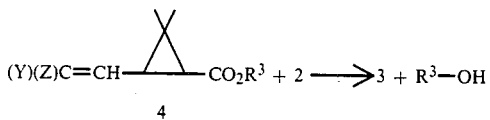

$(Y)(Z)C=CH-\overset{\times}{\underset{4}{\triangle}}-CO_2R^3 + 2 \longrightarrow 3 + R^3-OH$ Method A is a normal esterification procedure. In this method the appropriate carboxylic acid is converted into an activated derivative for esterification, generally the carboxylic acid bromide or chloride, which is then allowed to react under anhydrous conditions with the alcohol 2.

Method B involves a transesterification procedure. In this method the desired alcohol 2 exchanges with the existing alcohol moiety of an appropriate carboxylate 4 to give the ester of the desired alcohol. The reaction is driven to completion by removal by distillation of the alcohol $R^3$—OH formed from the displaced alcohol moiety. Thus, to facilitate the transesterification, $R^3$—OH should have a boiling point lower than that of alcohol 2. Frequently $R^3$ will be lower alkyl. The reaction is catalyzed by either acids or bases. Particularly desirable catalysts are the titanium alcoholates, for example, titanium isopropoxide.

Many of the intermediate acids from which the insecticidal esters of this invention are prepared are well known, and may be produced by methods in the literature of the art. Those acids not disclosed in the prior art may be prepared by analogous methods. Tetramethylcyclopropanecarboxylic acid and 1-(4-chlorophenyl)-2-methylpropyl-1-carboxylic acid may be prepared by methods outlined in *Synthetic Pyrethroids,* ACS Symposium Series, No. 42, M. Elliott, Ed., American Chemical Society, Washington, D.C., 1977, chapter 4, FIG. 4, page 48 and accompanying text; dihaloethenylcyclopropanecarboxylic acids, acids having the acyl group of formula II wherein each of Y and Z is a halogen atom, may be prepared by the method of Elliott et al., U.S. Pat. No. 4,024,163; (perhaloalkyl)ethenylcyclopropanecarboxylic acids, acids having the acyl group of formula II in which one of Y and Z is halogen and the other is a perhaloalkyl group, may be prepared by the method disclosed by Engel, U.S. Pat. No. 4,238,505; 1-(4-ethoxyphenyl)-2,2-dichlorocyclopropanecarboxylic acid may be prepared by the method of Holan and Walser, U.S. Pat. No. 4,220,591. The pertinent disclosures of the above four references are incorporated herein by reference.

The following examples illustrate methods of preparation for the novel alcohols and insecticidal esters of this invention. In the examples, all temperatures are in degrees Celsius, all pressures are in mm Hg, and reduced pressure for concentration of solvents was produced by a water aspirator unless otherwise specified.

EXAMPLE 1

Synthesis of 3-Phenylmethyl-1Indanone

A stirred solution of 63.4 g (0.627 mole) of dry diisopropylamine in 400 mL of tetrahydrofuran under an argon atmosphere was cooled to −65° C., and 343.0 mL (0.548 mole) of a 1.6M solution of n-butyllithium in hexane was added via a syringe. The reaction mixture was stirred at −65° C. for 0.5 hour, and a solution of 30.9 g (0.234 mole) of 1-indanone in 500 mL of tetrahydrofuran was added dropwise during 20 minutes. The reaction mixture was stirred for an additional 0.5 hour at −65° C., then for 2 hours without cooling. The reaction mixture was cooled to −20° C., and a solution of 50.0 g (0.293 mole) of phenylmethyl bromide in 125 mL of tetrahydrofuran was added dropwise rapidly. The reaction mixture was allowed to warm to ambient temperature, and was stirred for 16 hours, after which the reaction was quenched with 1 L of a saturated aqueous solution of sodium chloride and 1 L of aqueous 3N hydrochloric acid. The mixture was extracted with two portions of 500 mL each of diethyl ether. The ether extracts were combined and washed, first with two portions of 500 mL each of a saturated aqueous solution of sodium bicarbonate then with two portions of 500 mL each of a saturated aqueous solution of sodium metabisulfite. The organic layer was dried with magnesium sulfate, filtered, and the filtrate concentrated under reduced pressure to give approximately 60 g of residual oil. The oil was subjected to column chromatography on silica gel, eluting with methylene chloride, 1:19 ethyl acetatemethylene chloride, then ethyl acetate. The appropriate fractions were combined and concentrated to give a residue, which was subjected to rechromatography on silica gel. Elution was accomplished with heptane, 1:99 methylene chloride-heptane, 1:19 methylene chloride-heptane, 1:9 methylene chloride-heptane, 1:4 methylene chloride-heptane, 3:7 methylene chloride-heptane, 2:3 methylene chloride-heptane, and finally methylene chloride. The appropriate fractions were combined and concentrated under reduced pressure to give 21.0 g of 3-phenylmethyl-1-indanone, 96% pure by gas chromatography. The nmr spectrum was consistent with the proposed structure.

EXAMPLE 2

Synthesis of Cis,Trans-3-Phenylmethyl-1-Indanol

1. Use of aluminum isopropoxide/isopropanol

A stirred mixture of 2.0 g (0.009 mole) of 3-phenylmethyl-1-indanone and 1.8 g (0.009 mole) of aluminum isopropoxide in 40 mL of isopropanol was heated in a hot water bath, and by-product acetone was collected by distillation. Upon complete collection of acetone, the reaction mixture was cooled to ambient temperature, stirred for 16 hours, and concentrated under reduced pressure to give a residual oil. The oil was mixed with 125 mL of cold dilute hydrochloric acid, and the mixture was filtered to collect a solid. The solid was washed with cold hydrochloric acid and with cold water to give, after air drying, 1.7 g of cis,trans-3-phenylmethyl-1-indanol, 91% pure by gas chromatography, cis/trans ratio 61:39 by high pressure liquid chromatography.

2. Use of lithium aluminum hydride

A solution of 2 g (0.009 mole) of 3-phenylmethyl-1-indanone in 35 mL of tetrahydrofuran was added dropwise at 0° C. under a nitrogen atmosphere to a mixture of 0.21 g (0.0056 mole) of lithium aluminum hydride in 25 mL of tetrahydrofuran. The mixture was allowed to warm to ambient temperature, then was heated to 50° C. and stirred at that temperature for 16 hours. The reaction mixture was cooled, 50 mL of water was added, and the whole was extracted with diethyl ether. The ether layer was separated, washed, dried, and concentrated to give 1.60 g of cis,trans-3-phenylmethyl-1-indanol, 93% pure by gas chromatography, cis/trans ratio 89:11 by high pressure liquid chromatography.

3. Use of borane/tetrahydrofuran

A 1M solution of borane in tetrahydrofuran (3.3 mL, 0.0033 mole of borane) was mixed with 50 mL of tetrahydrofuran and 2 g (0.009 mole) of 3-phenylmethyl-1-indanone under a nitrogen atomosphere at −65° C. The mixture was allowed to warm to ambient temperature, and was stirred for 16 hours. The reaction mixture was cooled, diluted with water, and extracted with diethyl ether to give, from the ether extracts, 1.89 g of cis,trans-3-phenylmethyl-1-indanol, 70% pure by gas chromatography, cis/trans ratio 77:23 by high pressure liquid chromatography.

4. Use of ammonia borane

A mixture of 0.33 g (0.0108 mole) of ammonia borane, 2 g (0.009 mole) of 3-phenylmethyl-1-indanone, and 50 mL of isopropanol at 0° C. under a nitrogen atmosphere was allowed to come to ambient temperature, and was stirred for 16 hours to give, upon normal work-up, 1.63 g of cis,trans-3-phenylmethyl-1-indanol, 93% pure by gas chromatography, cis/trans ratio 69:31 by high pressure liquid chromatography.

EXAMPLE 3

Separation of Cis and Trans Isomers of Cis,Trans-3-Phenylmethyl-1-Indanol

The separation was accomplished by medium pressure liquid chromatography on a Waters Prep 500 chromatograph; eluent, 3:1 methylene chloride-heptane; flow rate, 250 mL/minute; quantity of sample for separation, 10.1 g. Collected fractions of eluate were monitored for cis and trans isomer content by high pressure liquid chromatography. Combination of appropriate fractions gave, after recrystallization from methylcyclohexane, 1.9 g of trans-3-phenylmethyl-1-indanol; 96% trans, 4% cis by high pressure liquid chromatography. Other fractions were combined to give 5.9 g of the cis indanol. The nmr spectra were consistent with the proposed structures.

trans-3-[(3-Fluorophenyl)methyl]-1-indanol (98% trans, 2% cis) and trans-3-[(4-fluorophenyl)methyl]-1-indanol (96% trans, 4% cis) were also prepared by the procedures described in Examples 1–3. The nmr spectra were consistent with the proposed structures.

Examples 4–11 illustrate preparation of the insecticidal esters of trans-3-substituted-1-indanol. The isomeric excess of the trans isomer in the indanyl moiety of the final product ester is the same as that for the trans-indanyl alcohol starting material.

EXAMPLE 4

Synthesis of Trans-3-Phenylmethyl-1-Indanyl 1R,Cis-3-(2,2-Dichloroethenyl)-2,2-Dimethylcyclopropanecarboxylate 1R,cis-3-(2,2-Dichloroethenyl)-2,2-dimethylcyclopropaneacarboxylic acid may be prepared by known methods, for example, the method described in Example 32 of U.S. Pat. No. 4,024,163, issued to Elliott et al., May 17, 1977. This same method is also described by P. E. Burt et al. in *Pestic. Sci.* 5, 791 (1974), at Sections 2.3 and 2.4, pp 793 and 794.

1R,cis-3-(2,2-dichloroethenyl)-2,2-dimethylcyclopropanecarbonyl chloride (0.52 g, 0.002 mole), which may be prepared by treatment of the corresponding carboxylic acid with oxalyl chloride, was added at 50° C. with stirring to a solution of 0.52 g (0.002 mole) of trans-3-phenylmethyl-1-indanol (95% trans, 5% cis) and 0.80 g (0.01 mole) of pyridine in 50 mL of toluene. The reaction mixture was stirred at 50° C.±4° C. for approximately 62 hours. The reaction mixture and 300 mL of heptane rinses were transferred to a separatory funnel, and the whole was washed with 100 mL of aqueous 2N hydrochloric acid, 100 mL of a saturated aqueous solution of sodium chloride, 125 mL of aqueous 2N sodium hydroxide, and finally, 75 mL of a saturated aqueous solution of sodium chloride. The organic layer was dried with magnesium sulfate, filtered, and the filtrate concentrated under reduced pressure to give a residual oil. The oil was subjected to column chromatography on silica gel, eluting with toluene. The appropriate fractions were combined and concentrated under reduced pressure to give 0.66 of trans-3-phenylmethyl-1-indanyl, 1R,cis-3-(2,2-dichloroethenyl)-2,2-dimethylcyclopropanecarboxylate. The nmr and ir spectra were consistent with the proposed structure.

Analysis calc'd for $C_{24}H_{24}Cl_2O_2$: C 69.41, H 5.12 Found: C 69.73, H 5.60.

EXAMPLE 5

Synthesis of Trans-3-Phenylmethyl-1-Indanyl Cis-3-(2-Chloro-3,3,3-Trifluoro-1-Propenyl)-2,2-Dimethylcyclopropanecarboxylate In the manner of Example 4, the reaction of 0.6 g (0.0027 mole) of trans-3-phenylmethyl-1-indanol (96% trans, 4% cis) and 0.704 g (0.0027 mole) of cis-3-(2-chloro-3,3,3-trifluoro-1-propenyl)-2,2-dimethylcyclopropanecarbonyl chloride (which may be prepared by method disclosed in U.S. Pat. No. 4,238,505, Example 7) in the presence of 0.214 g (0.0027 mole) of pyridine and 50 mL of toluene gave 0.75 g of trans-3-phenylmethyl-1-indanyl cis-3-(2-chloro-3,3,3-trifluoro-1-propenyl)-2,2-dimethylcyclopropanecarboxylate. The ir and nmr spectra were consistent with the proposed structure.

Analysis calc'd for $C_{25}H_{24}ClF_3O_2$: C 66.89, H 5.38, Found: C 66.25, H 5.62.

EXAMPLE 6

Synthesis of Trans-3-Phenylmethyl-1-Indanyl 1R,Trans-3-(2,2-Dichloroethenyl)-2,2-dimethylcyclopropanecarboxylate 1R,trans-3(2,2-Dichloroethenyl)-2,2-dimethylcyclopropanecarboxylic acid, from which the carbonyl chloride starting material of this example is made, may be prepared by the method disclosed in U.S. Pat. No. 4,024,163, Example 17.

In the manner of Example 4, the reaction of 0.614 g (0.0027 mole) of 1R,trans-3-(2,2-dichloroethenyl)-2,2-dimethylcyclopropanecarbonyl chloride and 0.6 g of trans-3-phenylmethyl-1-indanol (96% trans, 4% cis) in the presence of 0.214 g (0.0027 mole) of pyridine and 50 mL of toluene gave 0.57 g of trans-3-phenylmethyl-1-indanyl 1R,trans-3-(2,2-dichloroethenyl)-2,2-dimethylcyclopropanecarboxylate. The ir and nmr spectra were consistent with the proposed structure.

Analysis calc'd for $C_{24}H_{24}Cl_2O_2$: C 69.41, H 5.82, Found: C 68.86, H 5.60.

EXAMPLE 7

Synthesis of Trans-3-Phenylmethyl-1-Indanyl 1R,Cis-3-(2,2-Dibromoethenyl)-2,2-Dimethylcyclopropanecarboxylate 1R,cis-3-(2,2-Dibromoethenyl)-2,2-dimethylcyclopropanecarbonyl chloride may be prepared by the method described in U.S. Pat. No. 4,024,163, Example 27.

In the manner of Example 4, the reaction of 0.854 g (0.0027 mole) of the dibromoethenylcarbonyl chloride and 0.6 g (0.0027 mole) of trans-3-phenylmethyl-1-indanol (96% trans, 4% cis) in the presence of 0.214 g (0.0027 mole) of pyridine and 50 mL of toluene gave 0.83 g of trans-3-phenylmethyl-1-indanyl 1R,cis-3-(2,2-dibromoethenyl)-2,2-dimethylcyclopropanecarboxylate. The ir and nmr spectra were consistent with the proposed structure.

Analysis calc'd for $C_{24}H_{24}Br_2O_2$: C 57.17, H 4.79, Found: C 57.20, H 4.84.

EXAMPLE 8

Synthesis of Trans-3-[(4-Fluorophenyl)methyl]-1-Indanyl Cis-3-(2-Chloro-3,3,3-Trifluoro-1-Propenyl)-2,2-Dimethylcyclopropanecarboxylate In the manner of Example 4, the reaction of 1.00 g (0.004 mole) of trans-3-[(4-fluorophenyl)methyl]-1-indanol (96% trans, 4% cis) and 1.07 g (0.004 mole) of cis-3-(2-chloro-3,3,3-trifluoro-1-propenyl)-2,2-dimethylcyclopropanecarbonyl chloride in the presence of 0.32 g (0.004 mole) of pyridine and 50 mL of toluene gave 1.62 g of trans-3-[(4-fluorophenyl)methyl]-1-indanyl cis-3-(2-chloro-3,3,3-trifluoro-1-propenyl)-2,2-dimethylcyclopropanecarboxylate. The ir and nmr spectra were consistent with the proposed structure.

Analysis calc'd for $C_{25}H_{23}ClF_4O_2$: C 64.32, H 4.96, Found: C 64.55, H 5.13.

EXAMPLE 9

Synthesis of Trans-3-[(4-Fluorophenyl)methyl]-1-Indanyl Cis-3-(2,2-Dichloroethenyl)-2,2-Dimethylcyclopropanecarboxylate In the manner of Example 4, the reaction of 1.00 g (0.004 mole) of trans-3-[(4-fluorophenyl)methyl]-1-indanol (96% trans, 4% cis) and 0.93 (0.004 mole) of cis-3-(2,2-dichloroethenyl)-2,2-dimethylcyclopropanecarbonyl chloride in the presence of 0.32 g (0.004 mole) of pyridine and 50 mL of toluene gave 1.42 g of trans-3-[(4-fluorophenyl)methyl]-1-indanyl cis-3-(2,2-dichloroethenyl)-2,2-dimethylcyclopropanecarboxylate. The ir and nmr spectra were consistent with the proposed structure.

Analysis calc'd for $C_{24}H_{23}Cl_2FO_2$: C 66.52, H 5.34, Found: C 67.05, H 4.92.

EXAMPLE 10

Synthesis of Trans-3-[(3-Fluorophenyl)methyl]-1-Indanyl Cis-3-(2,2-Dichloroethenyl)-2,2-Dimethylcyclopropanecarboxylate In the manner of Example 4, the reaction of 1.00 g (0.004 mole) of trans-3-[(fluorophenyl)methyl]-1-indanol (98% trans, 2% cis) and 0.93 g (0.004 mole) of cis-3-(2,2-dichloroethenyl)-2,2-dimethylcyclopropanecarbonyl chloride in the presence of 0.32 g (0.004 mole) of pyridine and 50 mL of toluene gave 1.55 g of trans-3-[(3-fluorophenyl)methyl]-1-indanyl cis-3-(2,2-dichloroethenyl)-2,2-dimethylcyclopropanecarboxylate. The ir and nmr spectra were consistent with the proposed structure.

Analysis calc'd for $C_{24}H_{23}Cl_2FO_2$: C66.52, H 5.34, Found: C 66.95, H 5.37.

EXAMPLE 11

Synthesis of Trans-3-[(3-Fluorophenyl)methyl]-1-Indanyl Cis-3-(2-Chloro-3,3,3-Trifluoro-1-Propenyl)-2,2-Dimethylcyclopropanecarboxylate In the manner of Example 4, the reaction of 1.00 g (0.004 mole) of trans-3-[(3-fluorophenyl)methyl]-1-indanol (98% trans, 2% cis) and 1.07 g (0.004 mole) of cis-3-(2-chloro-3,3,3-trifluoro-1-propenyl)-2,2-dimethylcyclopropanecarbonyl chloride in the presence of 0.32 g (0.004 mole) of pyridine and 50 mL of toluene gave 1.52 g of trans-3-[(3-fluorophenyl)methyl]-1-indanyl cis-3(2-chloro-3,3,3-trifluoro-1-propenyl)-2,2-dimethylcyclopropanecarboxylate. The ir and nmr spectra were consistent with the proposed structure.

Analysis calc'd for $C_{25}H_{23}ClF_4O_2$: C 64.32, H 4.96, Found: C 64.76, 1 H 5.24.

In the method aspect of this invention, an effective insecticidal or acaricidal amount of the compound of formula I wherein R is other than hydrogen is applied to the locus where control is desired, i.e., to the insect or acarid itself or to the foliage or seeds of agricultural plants. The compounds are useful for the control of household, veterinary, and crop pests of the phylum Arthropoda, and may be applied as technical material or as formulated product. Typical formulations include compositions of the active ingredient in combination with an agriculturally acceptable carrier or extender, preferably with a surface active agent, and optionally with other active ingredient. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of active ingredient depending upon the particular agent used, the additives and carries used, other active ingredients, and the desired mode of application. With due consideration to these factors the active ingredient of a typical formulation may, for example, be suitably present at a concentration of about 0.01% up to about 99.5%, preferably 0.1% up to 90% or 95%, of the formulation. An agriculturally acceptable carrier may comprise about 99.5% by weight to as low as about 0.5% by weight of the formulation. Compatible surface active agents, if employed in a formulation, may be present at various concentrations, suitably in the range of 1 to 30% by weight of the formulation.

The formulation may be used as such or diluted to a desired use dilution with a diluent or carrier suitable for facilitating dispersion of the active ingredients. A concentration of the active ingredient in the use dilution may be in the range of 0.001% to about 50%, preferably up to about 10% by weight.

Many variations of spraying, dusting, and controlled or slow release compositions of a type known in the art may be used by substituting or adding an insecticidal compound or compounds of this invention into the compositions known or apparent to the art.

The insecticidal or acaricidal compounds of this invention may be formulated and applied with other compatible active agents including nematicides, insecticides, acaricides, fungicides, plant regulators, herbicides, fertilizers, and the like.

In applying these compounds, whether alone or with other agricultural chemicals, an effective insecticidal or acaricidal amount of the active ingredient must be applied. While the application rate will vary widely depending on the choice of compound, formulation, mode of application, plant species being protected, planted density and other like factors, a suitable use rate for agricultural crops may be in the range of 0.005 to 3 kg/ha, preferably 0.01 to about 1 kg/ha.

The insecticidal or acaricidal compounds of this invention were tested for pesticidal activity as described in Examples 12 and 13 below.

EXAMPLE 12

Insecticidal and Acaricidal Activity Foliar Application Procedure

Data for this test are reported in the table below as percent insect or mite mortality at a dosing rate of either 500 ppm (w/v) or 64 ppm (w/v).

The 500 ppm test solutions were prepared by diluting 2 mL of a 0.5% w/v solution of test compound in acetone to 20 mL with a stock solution of 1 drop/100 mL of octylphenoxypolyethoxyethanol emulsifier in water. The 64 ppm test solutions were prepared by first dissolving 37 mg of test compound in 250 mL of a 10% v/v acetone-water stock solution containing 1 drop/100 mL of octylphenoxypolyethoxyethanol to give a solution having 146 ppm (w/v) active ingredient, then diluting an aliquot of the 146 ppm solution with an appropriate amount of acetone-water-emulsifier stock solution to give a test solution containing 64 ppm (w/v) active ingredient.

Test organisms and techniques were as follows: The activity against Mexican bean beetle (*Epilachna varivestis* Muls.) and southern armyworm (*Spodoptera eridania* [Cram.]) was evaluated by spraying the leaves of pinto bean plants with the test solution until run-off, and infesting with 3rd instar larvae after the foliage has dried. The activity against the pea aphid (*Acrythosiphon pisum* [Harris]) was evaluated on broad bean plants the leaves of which were sprayed until run-off before infestation with adult aphids. The activity against twospotted spider mites (*Tetranychus urticae* [Koch]) was evaluated on pinto bean plants the leaves of which were dipped or sprayed with test solution after infestation with adult mits. To prevent escape of the insects from the test site, the complete test plant or the incised leaves were placed in capped paper cups. The tests were transferred to a holding room at 80° C. and 50% relative humidity for an exposure period of at least 48 hours. At the end of this time the dead and living insects were counted and the percent kill was calculated.

Included in these tests for comparison purposes were compounds which correspond in structure to the compounds of Examples 4, 5, 10, and 11 but differ from them in having a cis, rather than trans, alcohol moiety.

Results from these tests are summarized in the table below. The compounds having the cis alcohol moiety were, with certain exceptions, far inferior in activity to the corresponding trans alcohol compounds against the mites and each of the insect species.

Activity in Foliar Application Test

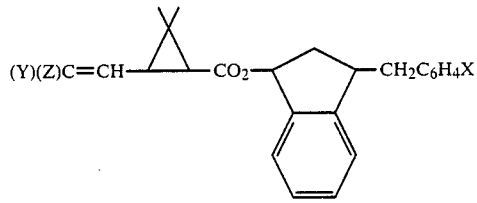

(Y)(Z)C=CH—△—CO$_2$—⬠—CH$_2$C$_6$H$_4$X

| Cpd of Ex. | Y | Z | X | Alcohol Moiety | Acid Moiety | % Kill @ (ppm) SAW | MBB | PA | TSM |
|---|---|---|---|---|---|---|---|---|---|
| — | Cl | Cl | H | cis | 1R,cis | 0(64) | 50(64) | 0(500) | 0(500) |
| 4 | Cl | Cl | H | trans | 1R,cis | 100(64) | 100(64) | 100(500) | 50(500) |
| — | Cl | CF$_3$ | H | cis | cis | 100(500) | — | 100(500) | 0(500) |
| 5 | Cl | CF$_3$ | H | trans | cis | 100(500) | — | 100(500) | 100(500) |
| 6 | Cl | Cl | H | trans | 1R,trans | 100(500) | 100(64) | 100(500) | 70(500) |
| 7 | Br | Br | H | trans | 1R,cis | 100(500) | 100(64) | 100(500) | 0(500) |
| 8 | Cl | CF$_3$ | 4-F | trans | cis | 100(500) | 100(64) | 80(500) | 60(500) |
| 9 | Cl | Cl | 4-F | trans | cis | 100(500) | 85(64) | 90(500) | 0(500) |
| — | Cl | Cl | 3-F | cis | cis | 95(500) | 0(64) | 65(500) | 0(500) |
| 10 | Cl | Cl | 3-F | trans | cis | 100(500) | 95(64) | 100(500) | 0(500) |
| — | Cl | CF$_3$ | 3-F | cis | cis | 30(500) | 35(64) | 100(500) | 0(500) |
| 11 | Cl | CF$_3$ | 3-F | trans | cis | 100(500) | 100(64) | 95(500) | 70(500) |

SAW — southern armyworm
MBB — Mexican bean beetle
PA — pea aphid
TSM — twospotted spider mite

EXAMPLE 13

Insecticidal Activity Topical Application Procedure

Two replicates of ten larvae of each test species were employed for each test compound. A 9 cm petri. dish lined with a piece of filter paper, and containing a food source was employed for each replicate. A one microliter droplet of a 5 mg/mL solution of test compound in acetone—a dosing rate equivalent to 5000 nanograms- /insect—was applied to the second or third dorsal thoracic segment of each larvae. The tests were read twenty-four hours after application of the toxicant solution, and the percent kill was determined.

The insect species employed were southern armyworm (*Spodoptera eridania* [Cram.]), Mexican bean beetle (*Epilachna varivestis* Muls.), and milkweed bug (*Oncopeltus faciatus* [Dallas]).

Included in these tests for comparison purposes were compounds which correspond in structure to the compounds of Examples 4, 5, 10 and 11 but differ from them in having a cis, rather than trans alcohol moiety.

The data from these tests are summarized in the table below. The compounds having the cis alcohol moiety were, with one exception against bean beetle, essentially inactive in these tests, and were far inferior to the corresponding trans compounds.

Activity in Topical Application Test

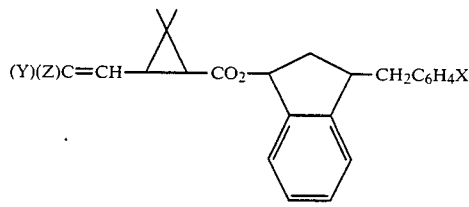

| Cpd of Ex. | Y | Z | X | Alcohol Moiety | Acid Moiety | % Kill @ 5000 mg/insect | | |
|---|---|---|---|---|---|---|---|---|
| | | | | | | SAW | MBB | MWB |
| — | Cl | Cl | H | cis | 1R,cis | 0 | — | 0 |
| 4 | Cl | Cl | H | trans | 1R,cis | 100 | — | 100 |
| — | Cl | $CF_3$ | H | cis | cis | 0 | 100 | 10 |
| 5 | Cl | $CF_3$ | H | trans | cis | 100 | 100 | 100 |
| 6 | Cl | Cl | H | trans | 1R,trans | 100 | 100 | 100 |
| 7 | Br | Br | H | trans | 1R,cis | 100 | 100 | 100 |
| 8 | Cl | $CF_3$ | 4-F | trans | cis | 75 | 75 | 70 |
| 9 | Cl | Cl | 4-F | trans | cis | 90 | 85 | 30 |
| — | Cl | Cl | 3-F | cis | cis | 0 | 0 | 0 |
| 10 | Cl | Cl | 3-F | trans | cis | 100 | 100 | 100 |
| — | Cl | $CF_3$ | 3-F | cis | cis | 0 | 0 | 0 |
| 11 | Cl | $CF_3$ | 3-F | trans | cis | 100 | 100 | 85 |

SAW — southern armyworm
MBB — Mexican bean beetle
MWB — milkweed bug

I claim:
1. A 3-substituted-1-indanol of the formula

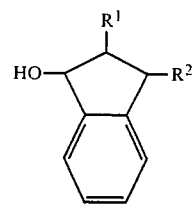

in which $R^1$ is hydrogen; $R^2$ is phenylmethyl, (lower alkyl-phenyl)methyl, or halophenylmethyl; and the 1,3-trans isomer is present in an isomeric excess over the 1,3-cis isomer of at least 50%.

2. The 3-substituted-1-indanol of claim 1 wherein $R^2$ is phenylmethyl, (lower alkyl-phenyl)methyl, fluorophenylmethyl, or chlorophenylmethyl.

3. The 3-substituted-1-indanol of claim 2 wherein $R^2$ is phenylmethyl, 3-fluorophenylmethyl, or 4-fluorophenylmethyl.

4. The 3-substituted-1-indanol of claim 1, 2, or 3 which consists essentially of the 1,3-trans isomer.

* * * * *